United States Patent [19]

Bailey et al.

[11] Patent Number: 5,145,786
[45] Date of Patent: Sep. 8, 1992

[54] PREENRICHED BROTH MEDIUM FOR THE SIMULTANEOUS SAMPLING OF FOODS FOR SALMONELLA AND LISTERIA

[75] Inventors: Joseph S. Bailey; Nelson A. Cox, both of Athens, Ga.

[73] Assignee: The United States of America as represented by the Secretary of Agriculture, Washington, D.C.

[21] Appl. No.: 586,116

[22] Filed: Sep. 21, 1990

[51] Int. Cl.$^5$ ............................................. C12N 1/20
[52] U.S. Cl. ............................ 435/252.4; 435/252.6; 435/252.8; 435/253.6
[58] Field of Search ................... 435/34, 253.6, 252.1, 435/252.4, 252.8

[56] References Cited
PUBLICATIONS

Manual of Clinical Microbiology, ASM, 1980, 3rd Ed., pp. 983-991.
Davis, Microbiology, 3rd Ed., p. 63.
Bailey, J. S. and Cox, N. A., Abstract Presented at the 1990 ASM Annual Meeting, Anaheim, Calif., May 13-17, 1990.

*Primary Examiner*—Douglas W. Robinson
*Assistant Examiner*—Jane A. Williams
*Attorney, Agent, or Firm*—M. Howard Silverstein; J. D. Fado; Janelle S. Graeter

[57] ABSTRACT

This invention relates to a preenrichment broth medium that allows for the simultaneous sampling for *Salmonella* and *Listeria* spp. The medium allows for the recovery of sublethally injured bacteria that would otherwise be overlooked by conventional techniques. The medium has utility in the food industry where the isolation and identification of these human enteropathogens is sought.

7 Claims, No Drawings

PREENRICHED BROTH MEDIUM FOR THE SIMULTANEOUS SAMPLING OF FOODS FOR SALMONELLA AND LISTERIA

BACKGROUND OF THE INVENTION

1. Field of the Invention

The present invention relates to chemical compositions of preenrichment broth and methods which allow the simultaneous sampling of food products for the human bacterial enteropathogens Salmonella and Listeria.

2. Description of the Prior Art:

Two to three million cases of Salmonella food poisoning are estimated to occur each year in the United States. Acute symptoms of this disorder include nausea, vomiting, diarrhea, cold chills, fever, and exhaustion. About 2,000-3,000 (0.1%) people die each year in the United States from Salmonella poisoning, with these victims usually being infants, the sick, and elderly. Seventeen hundred to 1800 cases of Listeria food poisoning are estimated to occur each year in the United States.

Acute symptoms include septicemic meningitis with mild flu-like symptoms reported in some cases. About 500 people (25 to 30%) people die each year in the United States from Listeria food poisoning, with the victims usually being the immunocompromised, pregnant women or neonates.

Poultry, red meat, seafood, eggs and any foods which contain these products or which come in contact with fecal material have the potential to carry the human bacterial enteropathogens Salmonella and Listeria. The challenge to a food microbiologist is to be able to recover small numbers of these select pathogens from food products which often contain large numbers of a variety of other bacteria. Recovery of sublethally injured Salmonella and Listeria is even more difficult. Heating, freezing, chemicals and other processing steps can sublethally injure or debilitate pathogenic bacteria in foods.

Traditional recover methods for foodborne Salmonella involve 5 basic steps:

1. Preenrichment—The initial step on which the food sample is enriched in a nonselective medium to restore injured Salmonella cells to a stable physiological condition.
2. Selective enrichment—A step in which the sample is further enriched in growth-promoting medium containing selectively inhibitory reagents. This medium allows a continued increase of Salmonella while simultaneously restricting proliferation of most other bacteria.
3. Selective plating—A step using solid selective media that restrict growth of bacteria other than Salmonella and provide visual recognition of pure, discrete colonies suspected to be *Salmonella*.
4. Biochemical screening—An elimination of most organisms other than Salmonella that also provides a tentative generic identification of Salmonella cultures.
5. Serotyping—A serological technique which provides a specific identification of cultures.

Listeria spp. have the ability to grow slowly at refrigerated temperatures. Historically, recovery methods for Listeria used a nonselective, nutrient, enrichment broth which when incubated at refrigeration temperatures for up to a month allowed the Listeria to grow while concurrently suppressing the growth of competitive microorganisms. The major disadvantage of this procedure is that it is very time consuming. Newer more timely procedures have been developed utilizing selected antibiotics, other chemical inhibitors, and elevated incubation temperatures. These procedures are quite similar to the 5 step procedure for recovery of Salmonella. However, unlike the Salmonella preenrichment step, the first stage of Listeria enrichment uses broth which contains antibiotics and chemicals and can interfere with the repair and growth of sublethally injured Listeria.

There are basic differences in Salmonella and Listeria which make simultaneous recovery of these two organisms seem incompatible. Salmonella are Gram negative bacteria while Listeria are Gram positive. Most chemical inhibitors or antibiotics which are active against Gram negative bacteria have little effect on Gram positive bacteria and vice versa.

Current procedures for recovery of Salmonella from food use either lactose broth or buffered peptone (BP) as preenrichment broths. Current procedures for recovery of Listeria from foods use either Listeria enrichment broth (LEB) or University of Vermont (UVM) broth as modified by the Food Safety Inspection Service of the USDA as preenrichment broths. Lactose and BP do not contain any chemical or antibiotic inhibitors. LEB and UVM contain both antibiotic and chemical inhibitors which favor the growth of Listeria while inhibiting the growth of competitive microorganisms which may be present in the foods. Sublethally injured Listeria may not repair and grow in the presence of these chemical inhibitors which have little effect on injured cells.

We found that in the presence of foods containing large numbers of extraneous microorganisms LEB did not contain sufficient buffers to prevent a rapid drop in the pH of the broth and injured cells could not be recovered. The primary disadvantage of the currently used first stage enrichment broths for Salmonella and Listeria are that the same broth cannot be used to simultaneously sample food and environmental samples for both of these pathogens and that the first stage enrichment for Listeria contains antibiotics and chemical inhibitors which can inhibit the recovery of sublethally injured Listeria.

It is estimated that in 1989 over 5 million Salmonella and 3 million Listeria analyses were run on food products in the United States. Many of these samples were analyzed for both Salmonella and Listeria. It can be seen that if samples could be analyzed simultaneously for Salmonella and Listeria there would be a tremendous saving in the media required, incubator space required, and food product needed for analyses. Therefor it is an object of the present invention to provide a preenrichment broth and method by which Salmonella and Listeria can be sampled simultaneously.

SUMMARY OF THE INVENTION

A medium and method for the simultaneous sampling of food products for Salmonella and Listeria is disclosed herein. To prevent the pH of the medium from rapidly dropping in the presence of extraneous microorganisms found in foods, this medium, universal preenrichment (UP) broth is highly buffered and low in carbohydrates. The medium must allow sublethally injured bacteria to resuscitate and multiply to sufficiently high numbers so that highly selective secondary enrichment media can be employed to help select the specific bacteria in question from a mixed bacterial background culture. From the universal preenrichment broth, secondary selective preenrichment broths which favor the growth of Salmonella or Listeria can be inoculated and subsequent protocols for the recovery of either Salmonella or Listeria can then be followed.

DETAILED DESCRIPTION OF THE INVENTION

The present invention may be practiced with any type of food product or environmental sample. Preferably, samples will be diluted at a rate of one gram or milliliter (ml) of food to 9 ml of UP broth. Environmental samples may use swabs diluted into 9.9 ml of UP broth. Preferably, UP broth samples will be incubated for 22 +/−2 hours at 35° C.

After incubation, 0.1 ml of the UP broth is transferred to 9 ml of the appropriate selective enrichment medium for either Salmonella or Listeria. Alternatively, 1 ml of the UP broth is transferred to 9 ml of the appropriate selective enrichment medium. The UP broth is designed such that the UP will serve as the first stage nonselective preenrichment and any approved Salmonella or Listeria recovery and detection protocols could subsequently be followed.

The composition of UP broth comprises tryptone, proteose peptone, glucose, sodium pyruvate, ferric ammonium citrate, sodium chloride, magnesium sulfate, and buffer salts. In a preferred embodiment, the composition comprises:

Tryptone...1 to 10 g/L
Proteose peptone...1 to 10 g/L
Glucose...0.2 to 1.0 g/L
Sodium pyruvate...0.2 to 2.0 g/L
Ferric ammonium citrate...0.1 to 2.5 g/L
Sodium chloride...1.0 to 5.0 g/L
$MgSO_4.7H_2O$...0.1 to 0.5 g/L,
Buffer salts.

In an especially preferred embodiment, the chemical formula for UP broth is as follows:

Tryptone...5 g
Proteose peptone...5 g
$KH_2PO_4$...15 g
$Na_2HPO4$...7 g
NaCl...5 g
Glucose...0.5 g
$MgSO_4.7H_2O$...0.25 g
Ferric ammonium citrate...0.5 g
Sodium pyruvate...0.2 g
Distilled water...1 L Mix all ingredients, bring to a boil, autoclave at 121° C. for 15 min. It is believed that other phosphates and buffers can be substituted for those listed as long as the buffering capacity remained the same or better and providing the level of glucose is kept at about 0.5 g.

The following examples are provided to more fully illustrate the effectiveness of the present invention, and are not to be taken as restrictive thereof. Four sets of situations and data which show the levels of Salmonella or Listeria present in UP after 24 hours incubation at 35° C.

EXAMPLE 1

Unstressed Salmonella and Listeria in Pure Culture

A 24 hour culture of Salmonella Typhimurium was diluted to the appropriate inoculum level (Table 1) and inoculated into both BP and UP broths. A 24 hour culture of Listeria monocytogenes was diluted to the appropriate inoculum level (Table 2) and inoculated into both UVM and UP broths. After 24 hours incubation at 35° C., the number of Salmonella or Listeria were determined in each broth.

TABLE 1

Growth of unstressed Salmonella in preenrichment broths incubated at 35° C. for 24 hours.

| Inoculum | Level[a] | Preenrichment | Counts[a] |
|---|---|---|---|
| Pure | $10^1$ | UP | $>10^9$ |
| Pure | $10^1$ | BP | $10^9$ |
| Pure | $10^3$ | UP | $>10^9$ |
| Pure | $10^3$ | BP | $>10^9$ |
| Mixed[b] | $10^1$ | UP | $10^9$ |
| Mixed | $10^1$ | BP | $10^9$ |

[a]Number of S. typhimurium per ml of enrichment broth.
[b]Mixed cultures had an equal mixture of Salmonella and Listeria in initial broth.

TABLE 2

Growth of unstressed Listeria in preenrichment broths incubated at 35° C. for 24 hours.

| Inoculum | Level[a] | Preenrichment | Counts[a] |
|---|---|---|---|
| Pure | $10^1$ | UP | $10^9$ |
| Pure | $10^1$ | UVM | $10^9$ |
| Pure | $10^3$ | UP | $10^9$ |
| Pure | $10^3$ | UVM | $>10^9$ |
| Mixed[b] | $10^1$ | UP | $10^6$ |
| Mixed | $10^1$ | UVM | $10^6$ |

[a]Number of L. monocytogenes per ml of enrichment broth.
[b]Mixed cultures had an equal mixture of Salmonella and Listeria in initial broth.

Salmonella in pure cultures or in equal mixtures of Listeria multiplied to at least $10^9$ per ml in both BP and UP broths within 24 hours incubation. Listeria in pure cultures multiplied to at least $10^9$ per ml of UVM or UP, or in equal mixtures of Salmonella multiplied to $10^6$ within 24 hours incubation. These counts exceed the minimum number of cells needed for transfer to secondary selective enrichment broths required to assure recovery from food samples.

EXAMPLE 2

Heat-injured Salmonella and Listeria in Pure Culture

Twenty-four hour cultures of Salmonella typhimurium were heated at 48° C. for 30 minutes and injury was determined by the difference in growth on BHI agar and BG sulfa+2% NaCl agar. Twenty-four cultures of Listeria monocytogenes were heated at 56° C. for 20 minutes and injury was determined by the difference in growth on BHI agar and BHI agar+4% NaCl.

Heat-injured S. typhimurium were diluted to the appropriate level (Table 3) and inoculated into BP or UP broths. Heat-injured L. monocytogenes were diluted to the appropriate level (Table 4) and inoculated into UVM or UP broths. After 24 hours incubation at 35° C., the number Salmonella or Listeria were determined in each broth.

TABLE 3

Growth of heat-injured Salmonella in preenrichment broths incubated at 35° C. for 24 hours.

| Inoculum | Level[a] | Preenrichment | Counts[a] |
|---|---|---|---|
| Pure | $10^1$ | UP | $10^8$ |
| Pure | $10^1$ | BP | $10^8$ |
| Pure | $10^2$ | UP | $10^8$ |
| Pure | $10^2$ | BP | $10^8$ |
| Mixed[b] | $10^1$ | UP | $10^8$ |
| Mixed | $10^1$ | BP | $10^8$ |
| Mixed | $10^2$ | UP | $10^8$ |

TABLE 3-continued

Growth of heat-injured Salmonella in preenrichment broths incubated at 35° C. for 24 hours.

| Inoculum | Level[a] | Preenrichment | Counts[a] |
|---|---|---|---|
| Mixed | $10^2$ | BP | $10^8$ |

[a]Number of S. typhimurium per ml of enrichment broth.
[b]Mixed cultures had an equal mixture of Salmonella and Listeria in initial broth.

TABLE 4

Growth heat-injured Listeria in preenrichment broths incubated at 35° C. for 24 hours.

| Inoculum | Level[a] | Preenrichment | Counts[a] |
|---|---|---|---|
| Pure | $10^1$ | UP | $10^8$ |
| Pure | $10^1$ | UVM | $10^6$ |
| Pure | $10^2$ | UP | $10^8$ |
| Pure | $10^2$ | UVM | $>10^6$ |
| Mixed[b] | $10^1$ | UP | $10^6$ |
| Mixed | $10^1$ | UVM | $10^5$ |
| Mixed | $10^2$ | UP | $10^6$ |
| Mixed | $10^2$ | UVM | $10^6$ |

[a]Number of L. monocytogenes per ml of enrichment broth.
[b]Mixed cultures had an equal mixture of Salmonella and Listeria in initial broth.

Heat-injured Salmonella in pure cultures or in equal mixture with of Listeria multiplied to at least $10^8$ per ml in both BP and UP broth within 24 hours incubation. Heat-injured Listeria in pure cultures multiplied to at least $10^6$ in UVM and to at least $10^8$ in UP within 24 hours, and in equal mixture with Salmonella multiplied to at least $10^5$ in UVM and at least $10^6$ in UP.

These counts exceed the minimum number of cells needed for transfer to secondary selective enrichment broths required to assure recovery from food samples.

EXAMPLE 3

Heat-injured Salmonella and Listeria in the known mixed microflora.

Twenty-four hour cultures of heat-injured S. typhimurium and L. monocyrogenes were diluted to the appropriate inoculum levels (Tables 5 & 6) and inoculated into either BP, UVM or UP along with approximately $10^7$ of each of the following competitive bacteria.

KNOWN MIXTURE OF BACTERIA:
- Klebsiella pneumoniae
- Citrobacter freundii
- Acinetobacter calcoaceticus
- Pseudomonas aeruginosa
- Staphylococcus aureus
- Enterobacter agglomerans
- Bacillus subtilis
- Proteus vulgaris After 24 hours incubation at 35° C., the number Salmonella or Listeria were determined in each broth.

TABLE 5

Growth of heat-injured Salmonella mixed microflora in preenrichment broth incubated at 35° C. for 24 hr.

| Inoculum[a] | Preenrichment | Count[a] |
|---|---|---|
| $10^1$ | UP | $10^7$ |
| $10^1$ | BP | $10^8$ |
| $10^2$ | UP | $10^8$ |
| $10^2$ | BP | $10^8$ |

[a]Number of S. Typhimurium per ml of enrichment broth.

TABLE 6

Growth of heat-injured Listeria in known mixed microflora in preenrichment broth incubated at 35° C. for 24 hr.

| Inoculum[a] | Preenrichment | Count[a] |
|---|---|---|
| $10^1$ | UP | $10^5$ |
| $10^1$ | UVM | $10^7$ |
| $10^2$ | UP | $10^5$ |
| $10^2$ | UVM | $10^7$ |

[a]Number of L. monocytogenes per ml of enrichment broth.

Heat-injured Salmonella multiplied to at least $10^7$ per ml in both BP and UP within 24 hours. Heat-injured Listeria multiplied to at least $10^5$ per ml in UP and $10^7$ per ml in UVM within 24 hours. These counts exceed the minimum number of cells needed for transfer to secondary selective enrichment broths required to assure recovery from food samples.

EXAMPLE 4

Heat-injured Salmonella and Listeria in Food Mixtures

Twenty-four hour cultures of heat-injured S. typhimurium and L. monocytogenes were diluted to the appropriate inoculum levels (Tables 7 & 8) and inoculated into either BP, UVM or UP which contained either chicken, hot dogs or Brie cheese at a ratio of 1 part food to 9 parts broth. After 24 hours incubation at 35° C., the number of Salmonella or Listeria were determined in each broth.

TABLE 7

Growth of Salmonella from different preenrichment food mixtures incubated at 35° C. for 24 hr.

| Food | Inoculum[a] | Preenrichment | Count[a] |
|---|---|---|---|
| Chicken | $10^1$ | UP | $10^6$ |
| Chicken | $10^1$ | BP | $10^7$ |
| Hot Dogs | $10^1$ | Up | $10^6$ |
| Hot Dogs | $10^1$ | BP | $10^7$ |
| Brie Cheese | $10^1$ | UP | $10^7$ |
| Brie Cheese | $10^1$ | BP | $10^7$ |

[a]Number of S. typhimruium per ml of enrichment broth.

TABLE 8

Growth of Listeria from different preenrichment food mixtures incubated at 35° C. for 24 hr.

| Food | Inoculum[a] | Preenrichment | Counts[a] |
|---|---|---|---|
| Chicken | $10^1$ | UP | $10^5$ |
| Chicken | $10^1$ | UVM | $10^5$ |
| Hot Dogs | $10^1$ | UP | $10^5$ |
| Hot Dogs | $10^1$ | UVM | $10^6$ |
| Brie Cheese | $10^1$ | UP | $10^6$ |
| Brie Cheese | $10^1$ | UVM | $10^6$ |

[a]Number of L. monocytogenes per ml of enrichment broth.

Heat-injured Salmonella multiplied to at least $10^6$ per ml in both BP and UP within 24 hours. Heat-injured Listeria multiplied to at least $10^5$ per ml in both UVM and UP within 24 hours. These counts exceed the minimum of $10^5$ within 24 hours. The foregoing material is illustrative of the present invention, and is not to be taken as restrictive thereof. The invention is defined by the following claims, with equivalents of the claims to be included therein.

It can be seen from the specification that there has been provided compositions and methods for the simultaneous sampling of Salmonella and Listeria. These compositions have special utility in the food industry for the detection of enteropathogens. The invention as described by the specific embodiment is not meant to limit its scope. Therefore it is envisioned and apparent that many alternatives and variations may be encompassed by the present invention. It is intended that the spirit and scope of this disclosure include such alternatives and variations.

We claim:

1. A preenrichment media comprising:
   Tryptone...1 to 10 g/L
   Proteose peptone...1 to 10 g/L
   Glucose...0.2 to 1.0 g/L
   Sodium pyruvate...0.2 to 1.0 g/L
   Ferric ammonium citrate...0.1 to 2.5 g/L
   Sodium chloride...1 to 5 g/L
   $MgSO_4 7H_2O$...0.1 to 0.5 g/L,
   buffer salts and IL distilled water.

2. The preenrichment media of claim 1, wherein the composition is in the form of a dry powder.

3. The preenrichment media of claim 1, wherein the composition additionally comprises water.

4. The preenrichment media of claim 1, wherein the buffer salts are:

$KH_2PO_4$ and $Na_2HPO_4$.

5. The preenrichment media of claim 5, wherein the composition comprises:
   Trystomer...5 g/L
   Proteose peptone...5 g/L
   Glucose...0.5 g/L
   Sodium pyruvate...0.2 g/L
   Ferric ammonium citrate...0.5 g/L
   Sodium chloride...5 g/L
   $M_gSO_4.7H_2O$...0.25 g/L,
   $KH_2PO_4$...15 g/L
   $Na_2HPO_4$...7 g/L
   Distilled water...IL 6. A method for preenriching and/or propogating in combination Salmonella and Listeria spp. comprising adding a sample containing Salmonella and Listeria spp. alone or in combination to a preenrichment media comprising:
   Tryptone...1 to 10 g/L
   Proteose peptone...1 to 10 g/L
   Glucose...0.2 to 1.0 g/L
   Sodium pyruvate...0.2 to 2.0 g/L
   Ferric ammonium citrate...0.1 to 2.5 g/L
   Sodium chloride...1 to 5 g/L
   $MgSO_4.7H_2O$...0.1 to 0.5 g/L
   Distilled water...IL, and
   buffer and salts.

7. The method of claim 6, wherein the preenrichment media comprises:
   Tryptone...5 g/L
   Proteose peptone...5 g/L
   Glucose...0.5 g/L
   Sodium pyruvate...0.2 g/L
   Ferric ammonium citrate...0.5 g/L
   Sodium chloride...5.0 g/L
   $MgSO_4.7H_2O$...0.25 g/L
   $KH_2PO_4$...15.0 g/L
   $Na_2HPO_4$...7.0 g/L.

* * * * *